United States Patent [19]

O'Dwyer

[11] Patent Number: 5,615,688
[45] Date of Patent: Apr. 1, 1997

[54] APNEA DETECTION DEVICE WITH A REMOTE MONITOR

[76] Inventor: Joseph E. O'Dwyer, 149 Old York Rd., Ringoes, N.J. 08551-1802

[21] Appl. No.: 654,163

[22] Filed: May 28, 1996

[51] Int. Cl.$^6$ ............................... A61B 5/08; A61B 5/113
[52] U.S. Cl. ..................... 128/716; 128/721; 128/723; 128/720
[58] Field of Search ........................... 128/716, 721, 128/723, 720

[56] References Cited

U.S. PATENT DOCUMENTS

| | | | |
|---|---|---|---|
| 3,782,368 | 1/1974 | Reibold | 128/721 X |
| 4,296,757 | 10/1981 | Taylor | 128/721 |
| 4,838,279 | 6/1989 | Fore | 128/721 |
| 4,846,462 | 7/1989 | Regnier et al. | 128/721 X |
| 4,895,162 | 1/1990 | Dolliver | 128/721 |
| 5,107,855 | 4/1992 | Harringto et al. | 128/721 |
| 5,295,490 | 3/1994 | Dodakian | 128/721 |
| 5,540,733 | 7/1996 | Testerman et al. | 128/721 X |

*Primary Examiner*—Angela D. Sykes
*Assistant Examiner*—Stephen D. Huang

[57] ABSTRACT

An apnea detection device with a remote monitor comprising a transmitter housing having a first portion and a second portion. The second portion has an unbiased contracted orientation with the second portion proximally situated with respect to the first portion. The second portion also has a biased extended orientation with the second portion distally situated with respect to the first portion. Also included is a strap for allowing the securement of the housing to a chest of an infant thus allowing the housing to be repeatedly biased coincidently with the breathing of the infant. A detection mechanism is included with the transmitter housing for monitoring biasing of the second portion associated with the respiration of the infant. Further included is a transmitter unit situated within the interior space of the first portion of the housing and connected to a small battery and the detection mechanism. The transmitter unit is adapted to transmit an activation signal upon the detection via the detection mechanism of an anomaly in the respiration of the infant. Finally, a receiver includes an alarm adapted to emit an audible signal upon the actuation thereof and a receiver unit adapted to actuate the alarm upon the receipt of the activation signal via the transmitter unit.

1 Claim, 3 Drawing Sheets

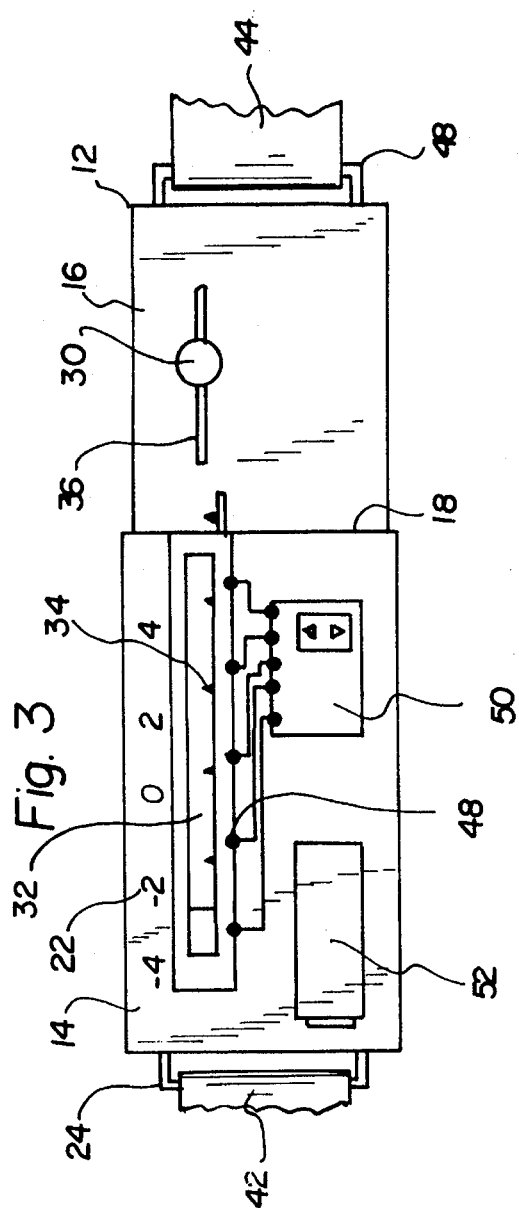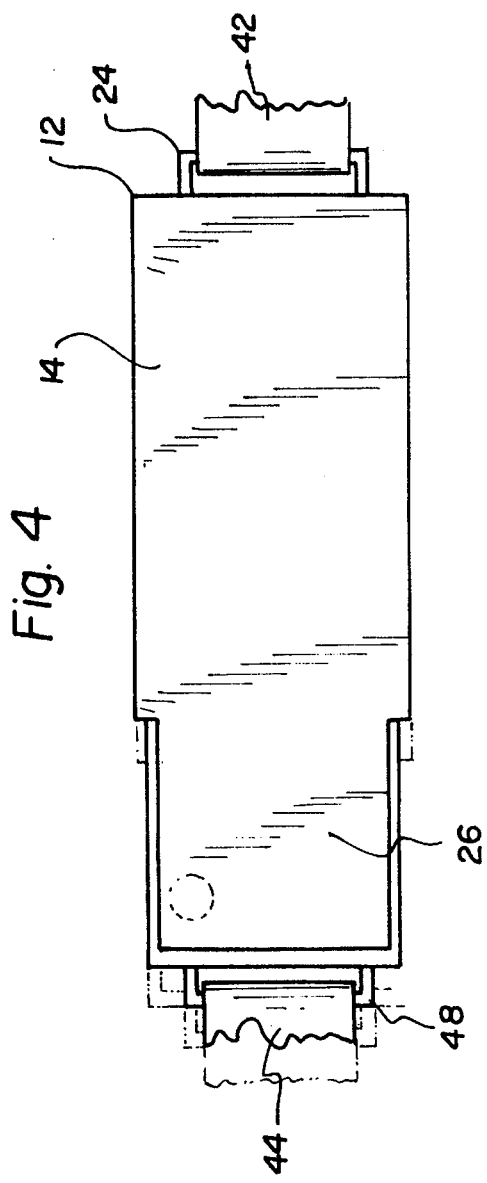

APNEA DETECTION DEVICE WITH A REMOTE MONITOR

BACKGROUND OF THE INVENTION

1. Field of the Invention

The present invention relates to a apnea detection device with a remote monitor and more particularly pertains to preventing the death of an infant due to an illness such as SIDS with an associated remote monitor.

2. Description of the Prior Art

The use of apnea prevention devices is known in the prior art. More specifically, apnea prevention devices heretofore devised and utilized for the purpose of preventing the death of an individual are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 5,107,855 to Harrington et al.; U.S. Pat. No. 5,241,300 to Buschmann; U.S. Pat. No. 5,295,490 to Dodakian; U.S. Pat. No. 4,657,026 to Tagg; U.S. Pat. No. 4,909,260 to Salem et al.; and U.S. Pat. No. Des. 353,202 to Hong.

In this respect, the apnea detection device with a remote monitor according to the present invention substantially departs from the conventional concepts and designs of the prior art, and in so doing provides an apparatus primarily developed for the purpose of preventing the death of an infant due to an illness such as SIDS with an associated remote monitor.

Therefore, it can be appreciated that there exists a continuing need for a new and improved apnea detection device with a remote monitor which can be used for preventing the death of an infant due to an illness such as SIDS with an associated remote monitor. In this regard, the present invention substantially fulfills this need.

SUMMARY OF THE INVENTION

In view of the foregoing disadvantages inherent in the known types of apnea prevention devices now present in the prior art, the present invention provides an improved apnea detection device with a remote monitor. As such, the general purpose of the present invention, which will be described subsequently in greater detail, is to provide a new and improved apnea detection device with a remote monitor which has all the advantages of the prior art and none of the disadvantages.

To attain this, the present invention essentially comprises a transmitter housing with a generally rectangular configuration. As best shown in FIGS. 1 & 2, the transmitter housing has a first portion and a second portion. The first portion includes a top face, a bottom face, and a thin periphery formed therebetween thus defining an interior space. Access is afforded to the interior space via an open side face. The first portion further includes a transparent window formed on the top face with indicia printed adjacent thereto. A closed coupling loop is formed on a side face of the housing opposite the open side face. A bottom planar extension is integrally formed with the bottom face and extended outwardly therefrom. The bottom planar extension resides within a plane in which the bottom face resides. The bottom planar extension includes a post coupled thereto. The post extends upwardly therefrom with a bulb formed on a top portion thereof. With reference still to FIGS. 1 & 2, the second portion of the housing includes a top face with a periphery integrally coupled thereto and depending therefrom. The second portion further includes a top planar extension integrally formed with the top face thereof. The top planar extension is adapted to be slidably inserted within the interior space of the first portion. A plurality of markers are printed on the top planar extension which are visible through the window of the first portion. As such, the markers work in conjunction with the indicia of the first portion for indicating a depth in which the top planar extension is inserted within the first portion. The second portion further includes a groove formed in the top surface thereof for accepting the post therein. Such a feature maintains a slidable relationship between the first portion and second potion. Also, another closed coupling loop is integrally coupled to the periphery of the second portion opposite the top planar extension thereof. The second portion has an unbiased contracted orientation with the second portion proximally situated with respect to the first portion. The second portion also has a biased extended orientation with the second portion distally situated with respect to the first portion. Also included is a stiff strap with a first extent having a first end coupled to the coupling loop of the first portion of the housing. A second end of the first extent has a pair of pile fasteners coupled thereto. The strap further has a second extent with a first end coupled to the coupling loop of the second portion of the housing. A second end of the second extent has a buckle coupled thereto. The strap thus allows the securement of the transmitter housing to a chest of an infant for allowing the housing to be repeatedly biased coincidently with the breathing of the infant. A conductive strip is situated on the top planar extension of the second portion of the housing. Working in conjunction with the strip is a plurality of linearly aligned contacts. The contacts are situated within the interior space of the first portion of the housing in linear alignment and in contact with the conductive strip. In operation, a decreasing amount of contacts are connected via the conductive strip upon the sliding of the second portion of the housing from an unbiased orientation to a biased orientation. Further included is a transmitter unit situated within the interior space of the first portion of the housing. The transmitter is connected to a small battery and the contacts. The transmitter unit is adapted to monitor the conductivity between subsequent contacts. Also, the transmitter is adapted to transmit an activation signal upon the detection of the strip connecting an amount of contacts greater than a predetermined amount for a predetermined amount of time. Finally, as shown in FIG. 6, a receiver includes a housing with a generally rectangular configuration. A speaker located within the receiver housing is adapted to emit an alarm upon the actuation thereof. A receiver unit also situated within the receiver housing is adapted to actuate the speaker upon the receipt of the activation signal via the transmitter unit.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved apnea detection device with a remote monitor which has all the advantages of the prior art apnea prevention devices and none of the disadvantages.

It is another object of the present invention to provide a new and improved apnea detection device with a remote monitor which may be easily and efficiently manufactured and marketed.

It is a further object of the present invention to provide a new and improved apnea detection device with a remote monitor which is of a durable and reliable construction.

An even further object of the present invention is to provide a new and improved apnea detection device with a remote monitor which is susceptible of a low cost of manufacture with regard to both materials and labor, and which accordingly is then susceptible of low prices of sale to the consuming public, thereby making such apnea detection device with a remote monitor economically available to the buying public.

Still yet another object of the present invention is to provide a new and improved apnea detection device with a remote monitor which provides in the apparatuses and methods of the prior art some of the advantages thereof, while simultaneously overcoming some of the disadvantages normally associated therewith.

Still another object of the present invention is to prevent the death of an infant due to an illness such as SIDS.

Lastly, it is an object of the present invention to provide a new and improved apnea detection device with a remote monitor comprising a transmitter housing having a first portion and a second portion. The second portion has an unbiased contracted orientation with the second portion proximally situated with respect to the first portion. The second portion also has a biased extended orientation with the second portion distally situated with respect to the first portion. Also included is a strap for allowing the securement of the housing to a chest of an infant thus allowing the housing to be repeatedly biased coincidently with the breathing of the infant. A detection mechanism is included with the transmitter housing for monitoring biasing of the second portion associated with the respiration of the infant. Further included is a transmitter unit situated within the interior space of the first portion of the housing and connected to a small battery and the detection mechanism. The transmitter unit is adapted to transmit an activation signal upon the detection via the detection mechanism of an anomaly in the respiration of the infant. Finally, a receiver includes an alarm adapted to emit an audible signal upon the actuation thereof and a receiver unit adapted to actuate the alarm upon the receipt of the activation signal via the transmitter unit.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cut away view of the transmitter housing of the present invention.

FIG. 4 is a rear elevational view of the transmitter housing of the present invention.

Similar reference characters refer to similar parts throughout the several views of the drawings.

DESCRIPTION OF THE PREFERRED EMBODIMENT

Figure 1:
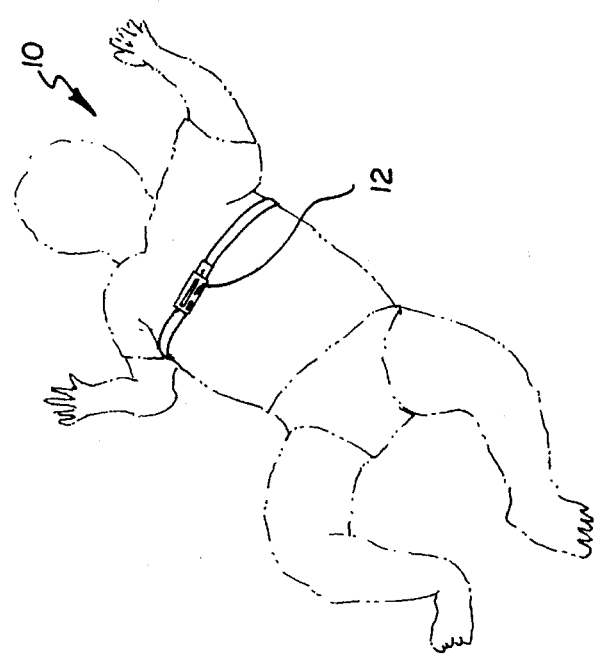
FIG. 1 is a perspective illustration of the preferred embodiment of the apnea detection device with a remote monitor constructed in accordance with the principles of the present invention.

With reference now to the drawings, and in particular to FIG. 1 thereof, a new and improved apnea detection device with a remote monitor embodying the principles and concepts of the present invention and generally designated by the reference numeral 10 will be described.

The present invention, the new and improved apnea detection device with a remote monitor, is comprised of a plurality of components. Such components in their broadest context include a transmitter housing, strap, conductive strip, contacts, transmitter, and receiver. Such components are individually configured and correlated with respect to each other so as to attain the desired objective.

Figure 2:
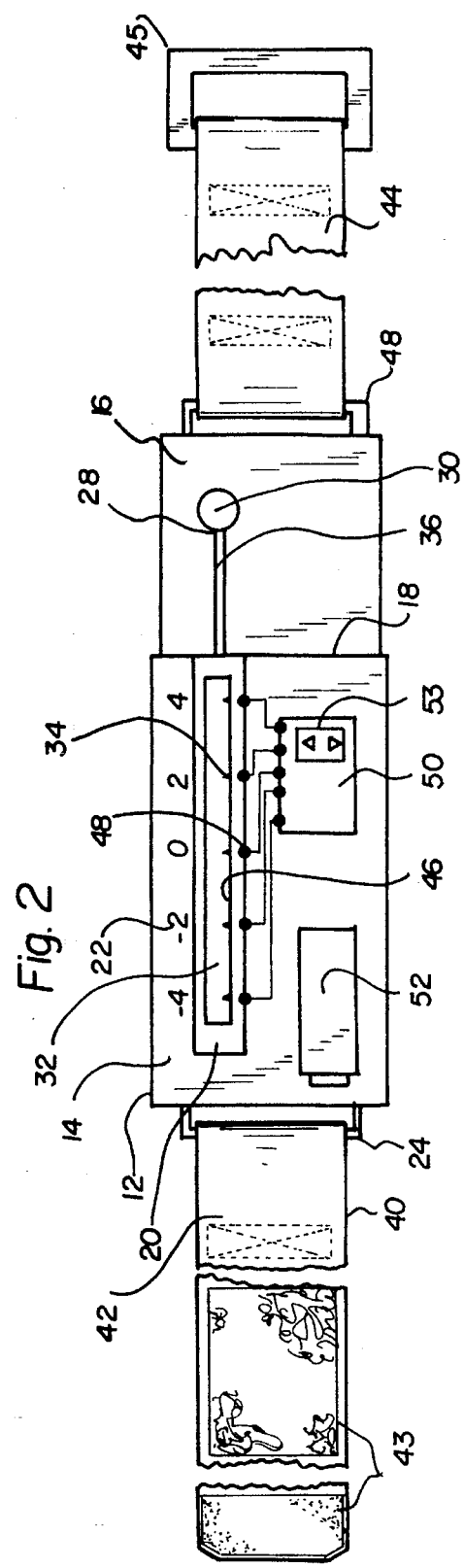
FIG. 2 is a front elevational view of the present invention.
Figure 5:
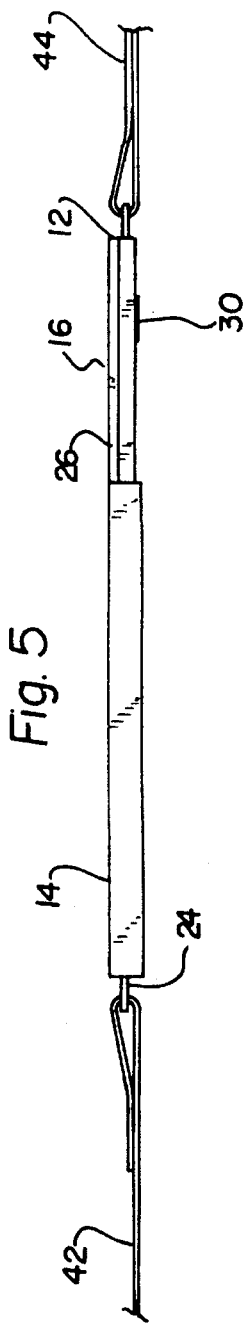
FIG. 5 is a side plan view of the transmitter housing of the present invention.

More specifically, it will be noted that the system 10 of the present invention includes a transmitter housing 12 with a generally rectangular configuration. As best shown in FIGS. 1 & 2, the transmitter housing has a first portion 14 and a second portion 16. The first portion includes a top face, a bottom face, and a thin periphery formed therebetween thus defining an interior space. Access is afforded to the interior space via an open side face 18. The first portion further includes a transparent window 20 formed on the top face with indicia 22 printed adjacent thereto. Such indicia includes a plurality of evenly spaced gauged numbers. A closed coupling loop 24 is formed on a side face of the transmitter housing opposite the open side face. A bottom planar extension 26 is integrally formed with the bottom face and extended outwardly therefrom. The bottom planar extension resides within a plane in which the bottom face resides. The bottom planar extension includes a post 28 coupled thereto. The post extends upwardly therefrom with a bulb 30 formed on a top portion thereof.

With reference still to FIGS. 1 & 2, the second portion of the housing includes a top face with a periphery integrally coupled thereto and depending therefrom. The second portion further includes a top planar extension 32 integrally formed with the top face thereof. The top planar extension is adapted to be slidably inserted within the interior space of the first portion. A plurality of markers 34 are printed on the top planar extension which are visible through the window of the first portion. As such, the markers work in conjunction with the indicia of the first portion for affording visual indication of the depth in which the top planar extension is inserted within the first portion. The second portion further includes a groove 36 formed in the top surface thereof for accepting the post therein. Such a feature maintains a slidable relationship between the first portion and second portion. Also, another closed coupling loop 38 is integrally coupled to the periphery of the second portion opposite the top planar extension thereof. The second portion has an unbiased contracted orientation with the second portion proximally situated with respect to the first portion. The second portion also has a biased extended orientation with the second portion distally situated with respect to the first portion. The bottom planar face ensures that the skin or clothing of the infant is not pinched or chafed by the movement of the first portion and second portion.

Also included is a stiff strap 40 with a first extent 42 having a first end coupled to the coupling loop of the first portion of the housing. A second end of the first extent has a pair of pile fasteners 43 coupled thereto. Ideally, a first pile fastener is sewn adjacent to the second end of the first extent of the strap and a second pile fastener is sewn adjacent thereto. The strap further has a second extent 44 with a first end coupled to the coupling loop of the second portion of the housing. A second end of the second extent has a buckle 45 coupled thereto. The strap thus allows the securement of the transmitter housing to a chest of an infant for allowing the housing to be repeatedly biased coincidently with the breathing of the infant. Ideally, each strap is approximately 11 cm in length.

A conductive strip 46 is situated on the top planar extension of the second portion of the housing.

Working in conjunction with the strip is a plurality of linearly aligned contacts 48. The contacts are situated within the interior space of the first portion of the housing in linear alignment and in contact with the conductive strip. In operation, a decreasing amount of contacts are connected via the conductive strip upon the sliding of the second portion of the housing from an unbiased orientation to a biased orientation.

Further included is a transmitter unit 50 situated within the interior space of the first portion of the housing. The transmitter is connected to a small battery 52 and the contacts. The transmitter unit is adapted to monitor the conductivity between subsequent contacts. Also, the transmitter is adapted to transmit an activation signal upon the detection of the strip connecting an amount of contacts greater than a predetermined amount for a predetermined amount of time. As an option, a pair of pivot switches is situated on the top face of the housing and is adapted to selectively increase or decrease the predetermined amount of contacts and the predetermined amount of time mentioned hereinabove.

Figure 6:
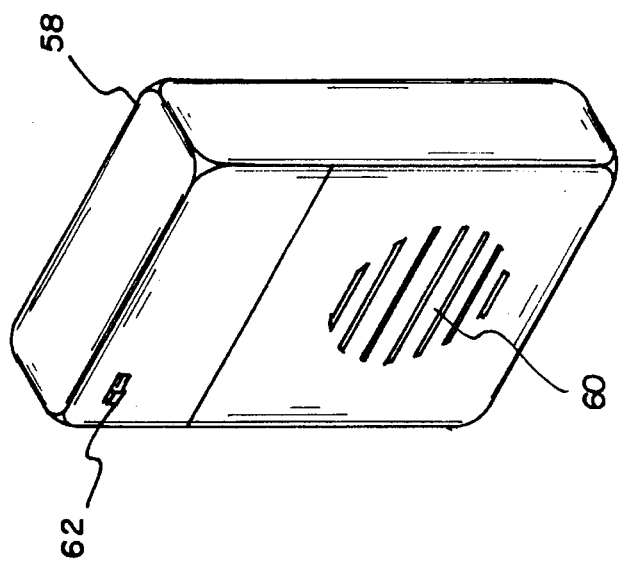
FIG. 6 is a perspective view of the receiver employed in the present invention.

Finally, as shown in FIG. 6, a receiver 58 includes a housing with a generally rectangular configuration. A speaker 60 located within the receiver housing is adapted to emit an alarm upon the actuation thereof. Optionally, an alarm selection button 62 is adapted to allow the receiver to selectively vibrate in combination with emitting an audible alarm upon the receipt of the activation signal via the transmitter unit. In use, the transmitter housing has a first portion and a second portion, wherein the second portion has an unbiased contracted orientation with the second portion proximally situated with respect to the first portion. The second portion further has a biased extended orientation with the second portion distally situated with respect the first portion. The strap is included for allowing securement of the transmitter housing to an infant. Such securement allows the housing to be repeatedly biased coincidently with the breathing of the infant. It is imperative that the plurality of linearly aligned contacts be situated within the first portion of the housing in linear alignment with the conductive strip which is situated on the second portion of the housing. By this structure, a decreasing amount of contacts are connected via the conductive strip upon the sliding of the second portion of the housing from the unbiased orientation to the biased orientation thereof or, in other words, an increasing amount of contacts are connected via the conductive strip upon the sliding of the second portion of the housing from the biased orientation to the unbiased orientation thereof. The transmitter unit is connected to a small battery and the contacts such that the transmitter unit is adapted to transmit an activation signal upon the detection of the strip connecting an amount of contacts greater than a predetermined amount for a predetermined amount of time. Since an increasing amount of contacts are connected via the conductive strip upon the sliding of the second portion of the housing from the biased orientation to the unbiased orientation thereof, it is apparent that when an infant stops breathing, the housing will assume the unbiased orientation which means an increased amount of contacts are connected via the conductive strip. This allows the transmitter to transmit an activation signal which, in turn, actuates the receiver.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved apnea detection device with a remote monitor comprising, in combination:

a transmitter housing with a generally rectangular configuration having a first portion and a second portion, the first portion including a top face, a bottom face, and a thin periphery formed therebetween defining an interior space with access afforded thereto via an open side face, the first portion further including a transparent window formed on the top face with indicia printed adjacent thereto including a plurality of evenly spaced numbers, a closed coupling loop formed on a side face opposite the open side face, and a bottom planar extension integrally formed with the bottom face and extended outwardly therefrom within a plane in which the bottom face resides, the bottom planar extension including a post coupled thereto and extended upwardly therefrom with a bulb formed on a top portion thereof, the second portion of the housing including a top face with a periphery integrally coupled thereto and depending therefrom, the second portion further including a top planar extension integrally formed with the top face thereof with the top planar extension adapted to be slidably inserted within the interior space of the first portion wherein a plurality of markers printed thereon are visible through the window of the first portion so as to work in conjunction with the indicia of the first portion for indicating a depth the top planar extension is inserted within first portion, the second portion further including a groove formed in the top surface thereof for accepting the post therein so as to maintain a slidable relationship between the first portion and second portion and another closed coupling loop integrally coupled to the periphery of the second portion opposite the top planar extension thereof, wherein the second portion has an unbiased contracted orientation with the second portion proximally situated with respect to the first portion and a biased extended orientation with the second portion distally situated with respect to the first portion;

a stiff strap with a first extent having a first end coupled to the coupling loop of the first portion of the housing and a second end with a pair of pile fasteners coupled thereto, the strap further having a second extent with a first end coupled to the coupling loop of the second portion of the housing and a second end with a buckle coupled thereto, whereby the strap allows securement of the housing to a chest of an infant thus allowing the housing to be repeatedly biased coincidently with breathing of the infant;

a conductive strip situated on the top planar extension of the second portion of the housing;

a plurality of linearly aligned contacts situated within the interior space of the first portion of the housing in linear alignment and contact with the conductive strip, whereby a decreasing amount of contacts are connected via the conductive strip upon the sliding of the second portion of the housing from an unbiased orientation to a biased orientation;

a transmitter unit situated within the interior space of the first portion of the housing and connected to a small battery and the contacts, the transmitter unit adapted to monitor the conductivity between subsequent contacts and further transmit an activation signal upon the detection of the strip connecting an amount of contacts less than a predetermined amount;

a receiver including a housing with a generally rectangular configuration, a speaker adapted to emit an alarm upon the actuation thereof, and a receiver unit adapted to actuate the speaker upon the receipt of the activation signal via the transmitter unit; and a pair of switches situated on the top face of the housing adapted to selectively increase or decrease the predetermined amount of contacts and the predetermined amount of time.

\* \* \* \* \*